United States Patent [19]

Knight et al.

[11] Patent Number: 5,019,097
[45] Date of Patent: May 28, 1991

[54] CORNEAL ONLAY LENSES AND METHODS FOR ATTACHING SAME

[75] Inventors: Patricia M. Knight, Laguna Niguel; Robert C. Bishop, San Marino, both of Calif.

[73] Assignee: Allergan, Inc., Irvine, Calif.

[21] Appl. No.: 440,975

[22] Filed: Nov. 22, 1989

[51] Int. Cl.$^5$ .............................................. A61F 2/14
[52] U.S. Cl. ................................................... 623/5
[58] Field of Search ......................................... 623/4–6

[56] References Cited

U.S. PATENT DOCUMENTS

| | | | |
|---|---|---|---|
| 2,714,721 | 8/1955 | Stone, Jr. | 623/5 |
| 3,866,249 | 2/1975 | Flom | 623/6 |
| 4,150,471 | 4/1979 | Richards et al. | 29/450 |
| 4,338,687 | 7/1982 | Rainin | 623/6 |
| 4,346,482 | 8/1982 | Tennant et al. | 623/6 |
| 4,468,820 | 9/1984 | Uhler et al. | 623/6 |
| 4,547,914 | 10/1985 | Castleman | 623/6 |
| 4,573,998 | 3/1986 | Mazzocco | 623/6 |
| 4,615,702 | 10/1986 | Koziol et al. | 623/6 |
| 4,646,720 | 3/1987 | Peyman et al. | 623/5 X |
| 4,668,446 | 5/1987 | Kaplan et al. | 623/6 X |
| 4,693,715 | 9/1987 | Abel, Jr. | 623/5 |
| 4,737,322 | 4/1988 | Bruns et al. | 623/6 X |
| 4,772,283 | 9/1988 | White | 623/5 |
| 4,790,846 | 12/1988 | Christ et al. | 623/6 |
| 4,810,082 | 3/1989 | Abel, Jr. | 623/5 X |
| 4,834,751 | 5/1989 | Knight et al. | 623/6 |
| 4,842,599 | 6/1989 | Bronstein | 623/5 |
| 4,923,467 | 5/1990 | Thompson | 623/4 X |

FOREIGN PATENT DOCUMENTS 0125361 11/1984 European Pat. Off. .
8400883 3/1984 PCT Int'l Appl. ............... 623/6

OTHER PUBLICATIONS

Prosthokeratoplasty, Hernando Cardona, M.D., (1983), Cornea, vol. 2, No. 3, pp. 179–183, 623–625.

Primary Examiner—Ronald Frinks
Attorney, Agent, or Firm—Gordon L. Peterson; Frank J. Uxa, Jr.

[57] ABSTRACT

Lenses and methods of lens attachment are disclosed which provide for highly effective, e.g., secure, attachment of the lens to the patient's cornea. Lenses are configured which are particularly adapted to be overlaid with corneal tissue to protect the lenses from forces parallel to the radial axis of the lens and generally parallel to the anterior surface of the lens optic.

39 Claims, 3 Drawing Sheets

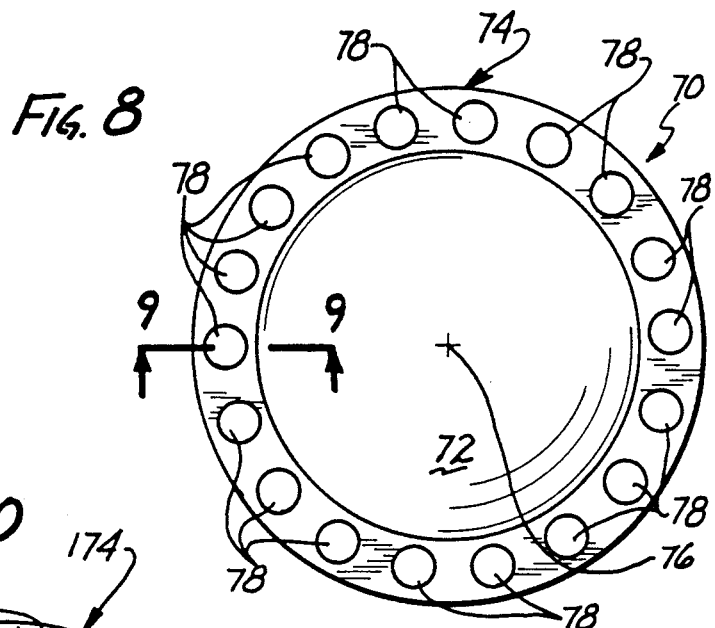
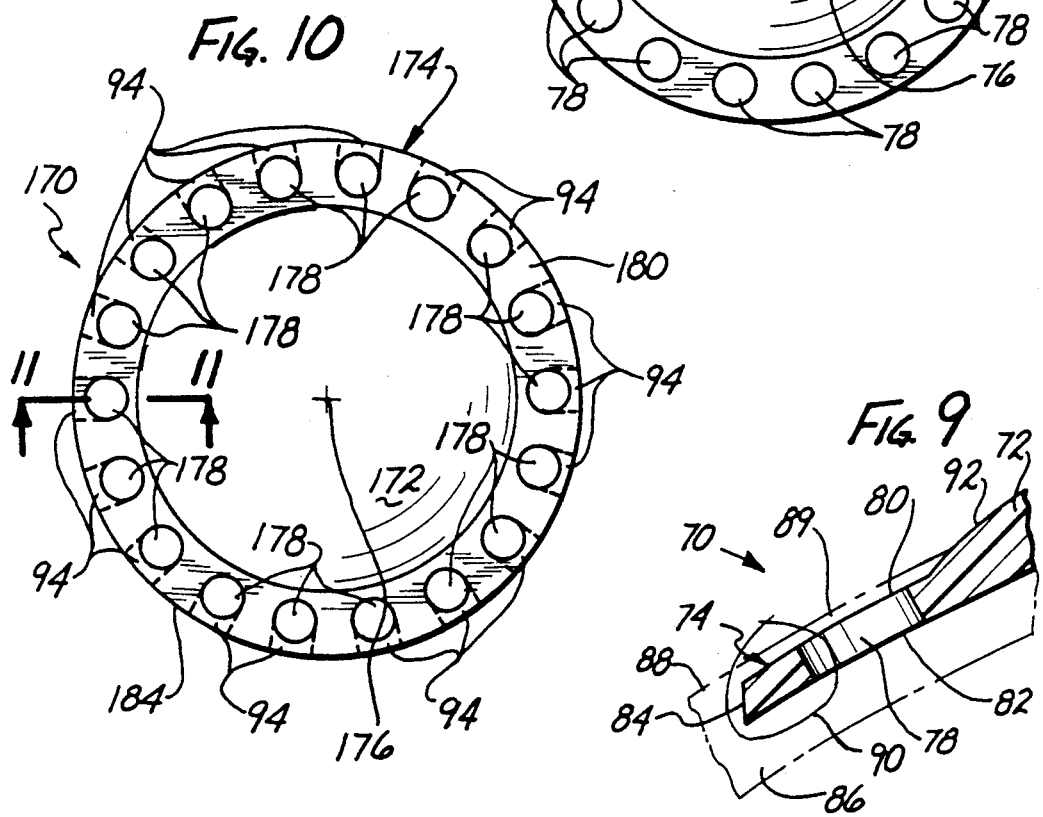
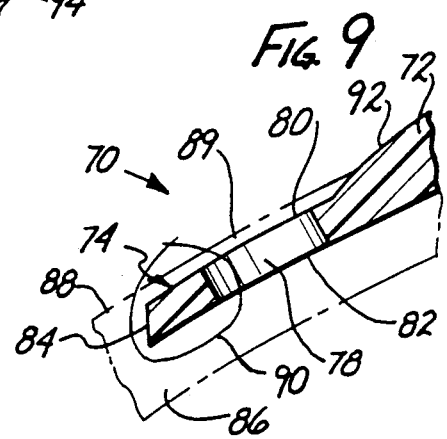
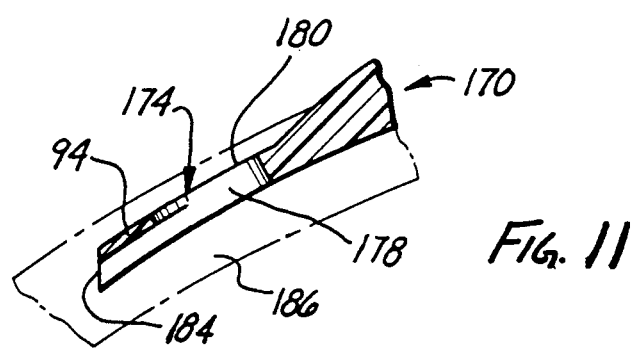

CORNEAL ONLAY LENSES AND METHODS FOR ATTACHING SAME

BACKGROUND OF THE INVENTION

The present invention relates to corneal onlay lenses and to methods for attaching such lenses to the cornea. More particularly, the invention relates to lenses and to lens attachment methods in which the lens has increased resistance to being removed.

Currently, epikeratophikia lenses are attached to the cornea by tucking the tapered lens edge into a circular groove cut into the peripheral cornea. A suture is then passed through the lens and cornea to attach the lens. With time, scarring occurs in this peripheral groove which functions to permanently fixate the lens to the cornea. The suture can then be removed.

This approach to permanently fixating epikeratophikia lenses has various limitations or problems, in particular, if the lens is made of certain synthetic materials. For example, the desired scarring may not occur. Also, suturing may not be practical because of the mechanical strength of the lens material or for other reasons. Thus, it would be advantageous to have lens designs and methods of lens attachment which do not present such difficulties.

Peyman et al U.S. Pat. No. 4,646,720 discloses a corneal onlay lens including at least one opening for the diffusion of nutrients from the recipient's cornea. These openings, which can be located anywhere through the lens, do not play any direct role in attaching the lens to the cornea and must remain open in order to provide for the flow of nutrients.

Abel, Jr., U.S. Pat. No. 4,693,715 discloses a corneal implant which includes a series of through bores for receiving sutures to couple the implant to the cornea. These through bores extend from the top or anterior surface of the lens to the periphery of the lens. In place, the periphery of the lens abuts the cornea, but is not covered by any corneal tissue.

H. Cardona, in an article entitled "Prosthokeratoplasty", Cornea 2:pp 179-183, 1983, describes a keratoprosthesis including an optical cylinder made of methyl methacrylate with a contact lens glued to its anterior surface, and a TEFLON ring with multiple small and large openings. This TEFLON skirt is sutured over the anterior surface of the cornea. The openings in the TEFLON ring are there to allow recipient corneal tissue to grow through. This system is quite cumbersome and, since the TEFLON (polytetrafluoroethylene) ring is entirely over the cornea, tends to be easily moved out of position. A lens and attachment method with which provides for more secure lens attachment is clearly needed.

SUMMARY OF THE INVENTION

New lenses and methods of attaching lenses to corneas have been discovered. The present lenses are structured to allow secure attachment or fixation to the cornea. Thus, the risk of the lens being accidentally moved out of position or even removed from the eye is reduced. These lenses are configured so that corneal tissue can be placed in overlaying relationship to the peripheral portion of the lenses so as to form a "mechanical interlock" to hold the lens in place. This holding effect is useful against forces parallel to the optical axis of the lens as well as against forces which are generally parallel to the anterior surface of the lens. The present lens attachment methods are useful with the lenses noted above, as well as with other lenses. In any event, the present invention provides highly effective, e.g., secure, epikeratophikia lens attachment.

A lens device for attachment to the cornea of a patient is provided which comprises an optic and a flange or wing extending radially from the optic. The optic, preferably centrally located, is configured for correction of the patient's vision. In one embodiment, the flange has a first posterior surface, a second anterior surface, a third surface adjacent the first posterior surface away from the optic, and a fourth surface adjacent the second anterior surface away from the optic. The third and fourth surfaces define a generally V-shaped flute extending generally outwardly from the radial axis of the lens device. The area of at least one of the third and fourth surfaces is preferably larger than the area of at least one surface in the flange parallel to the optical axis of the lens device. More preferably, the areas of both the third and fourth surfaces are larger than the area of at least one surface in the flange parallel to the radial axis of the lens device. In a particularly useful embodiment, the surface formed between the outer edges of the third and fourth surfaces has an area larger than the area of at least one surface in the flange parallel to the optical axis of the optic. The angle defined by this V-shaped flute is preferably less than about 90°. The third surface is overlaid with corneal tissue to provide for secure attachment when this lens is attached to a patient's cornea. In a particularly useful embodiment, both the third surface and the second anterior surface of the flange are overlaid with corneal tissue to provide for secure attachment. The lens device is placed relative to the cornea so that the V-shaped flute is substantially filled with corneal tissue. The lens device is thus mechanically "locked" in place for secure attachment to the cornea.

In another embodiment, the flange has a first posterior surface, a second anterior surface and a third surface away from the optic and joined to the second anterior surface. This third surface preferably has an area larger than the area of at least one surface in the flange parallel to the optical axis of the lens device. A fourth surface is provided which, together with the first posterior surface, forms a generally V-shaped flute extending generally toward the optical axis. This generally V-shaped flute, which preferably defines an angle of less than about 90°, provides substantial advantages, e.g., in securing the lens device to the cornea. For example, not only can the corneal tissue be laid over the top of the second anterior surface of the flange, but also the lens device can be placed so that corneal tissue substantially fills the V-shaped flute defined by the fourth surface and the first posterior surface of the flange. This "double locking" arrangement is particularly effective in securing the lens device to the cornea.

The generally V-shaped flute structures of the embodiments of the present invention noted above reduce, and in certain instances eliminate, the need for suturing the lens device to the cornea. In any event, whether or not suturing is used, such lens devices can be securely attached or affixed to the cornea and are resistant to being moved by forces parallel to the radial axis of the optic or the lens device, and substantially parallel to the anterior surface of the optic.

A further embodiment of the present invention involves a lens device with a flange which has at least one through hole or fenestration sized and adapted to provide growth of corneal tissue therethrough. Preferably, a plurality of such through holes are provided, more preferably substantially uniformly spaced on, e.g., around, the flange. The lens device preferably has an outer periphery and includes one area per through hole which has reduced strength, relative to the remainder of the solid flange, and which is located between the through hole and the outer periphery of the flange. For example, this area of reduced strength may involve an area in which the flange has reduced thickness relative to the average thickness of the solid flange. Such reduced strength areas are effective in situations where it is desired to remove the lens device, e.g., after a period of use. For example, one or more of these reduced strength areas can be cut or otherwise ruptured to facilitate the removal of the lens from the cornea.

An additional embodiment of the present invention involves a lens device having a flange with increased unit strength relative to the optic. At least one through hole or fenestration is located in the flange. This through hole is sized and adapted to provide for growth of corneal tissue therethrough. Preferably, a plurality of such through holes is provided in the flange. These through holes, which are more preferably substantially evenly spaced on, e.g., around, the flange, act to provide growth paths for corneal tissue once the flange is placed in association with the cornea.

The term "unit strength" refers to the strength of an element having a standard size and configuration. In other words, the flange of the embodiment described immediately above is stronger than a similarly sized and configured flange made of the same material from which the optic is produced.

The use of a relatively strong flange with one or more through holes located therein provides substantial advantages. Although the through holes are adapted to provide for growth of corneal tissue therethrough, they also may be useful for suturing the lens device to the cornea. Thus, having a relatively strong flange allows the surgeon more freedom or flexibility in suturing the lens device to the cornea.

In one particularly useful embodiment, the flange is originally made of the same material from which the optic is made. In this arrangement, the flange may be selectively modified, e.g., subjected or exposed to radiation, such as ultraviolet light or gamma-ray radiation, to selectively cross-link the material making up the flange so as to provide a flange having increased unit strength relative to the optic. This embodiment is particularly applicable if the lens device is originally made from one or more hydrogel-forming materials.

Various of the features outlined above with respect to individual embodiments of the present invention can be used in combination with each other. Such combination lens devices are within the scope of the present invention.

In a further aspect of the present invention, a method of attaching a lens device to the cornea of a patient is provided. This method comprises placing a lens device, having a radial axis, an optic and a radially extending flange in association with the cornea so that corneal tissue overlays at least a portion of the flange, and preferably substantially none of the optic. This method can be advantageously used to attach a lens device in which the flange has a first posterior surface and a second anterior surface at least one of which is adjacent a third surface away from the optic. The area of this third surface is larger than the area of at least one surface in the flange parallel to the radial axis of the lens device. This method is particularly applicable with regard to the other lens devices described herein. The present method preferably provides for association between the lens device and the cornea so that the lens device has increased resistance to being moved in response to a force applied in a direction parallel to the optical axis of the lens device and to a force applied in a direction generally parallel to the anterior surface of the optic of the lens device. Such resistance is increased relative to a similar lens associated with a cornea in a similar manner except that no corneal tissue overlays at least a portion of the flange of a similar lens device.

The present methods preferably further include preparing the cornea to receive a portion of the lens device prior to placing the lens device in association with the cornea. In many instances, this preparation involves forming annular groove or grooves of a desired configuration in the cornea. Corneal tissue may be removed at the location of the groove or grooves to better accommodate the flange of the lens device. Forming such annular groove or grooves and removing corneal tissue may be accomplished using conventional techniques and instruments well known in the art. In addition, the central portion of the cornea may be removed, e.g., abraded away, using conventional techniques and instruments well known in the art.

Although both naturally occurring and synthetic materials may be used to produce the present lens devices, it is particularly useful to provide a lens device constructed of one or more synthetic materials, e.g., polymeric materials. The use of synthetic materials allows for more flexibility in configuring the lens device to suit the requirements of the particular application involved. In addition, various features of the present invention are particularly applicable to the structural characteristics and properties of various synthetic materials. Both the optic and the flange or wing of the present lens devices are preferably made of the same basic material. Exemplary synthetic materials that can be used include methacrylates such as polymethyl methacrylate and hydroxyethyl methacrylate, silicones, styrenes, glasses, lower alkyl butyrates, silicone-acrylate copolymers, fluorocarbons such as polytetrafluoroethylene, polyolefins such as polyethylene and polypropylene, polyethylene terephthalate, poly N-vinyl pyrrolidone, polyurethanes and mixtures thereof. Materials which form hydrogels and/or are maintained as hydrogels under normal use conditions of the lens device, e.g., in the human eye, are particularly applicable.

These and other aspects and advantages of the present invention are set forth in the following detailed description and claims, particularly when considered in conjunction with the accompanying drawings in which like parts bear like reference numerals.

BRIEF DESCRIPTION OF THE DRAWINGS

FIG. 8 is a top plan view of an additional lens device according to the present invention.

FIG. 9 is a cross-sectional view taken along line 9—9 in FIG. 8 showing the lens device attached to a cornea.

FIG. 10 is a top plan view of a further lens device according to the present invention.

FIG. 11 is a cross-sectional view taken along line 11-11 of FIG. 10 showing the lens device attached to a cornea.

DETAILED DESCRIPTION OF THE DRAWINGS

Figure 1:
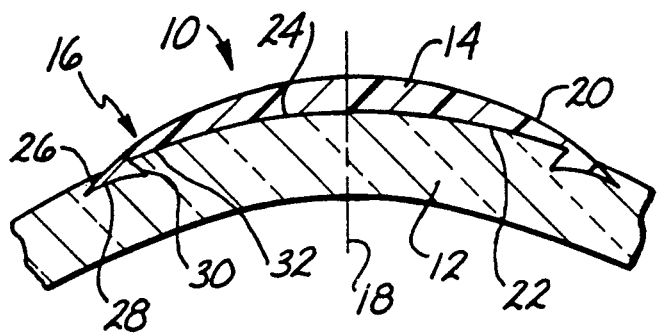
FIG. 1 is a cross-sectional view of a lens device according to the present invention shown attached to a cornea.
Figure 3:
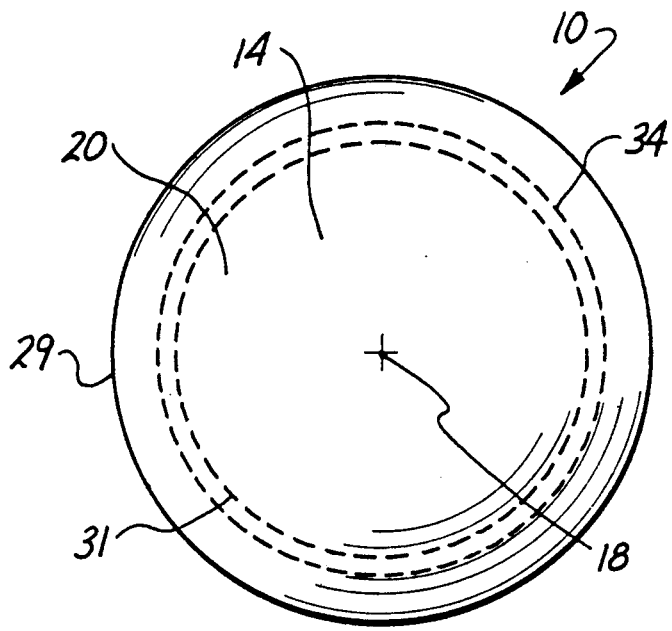
FIG. 3 is a top elevational view of the lens device shown in FIG. 1.
Figure 4:
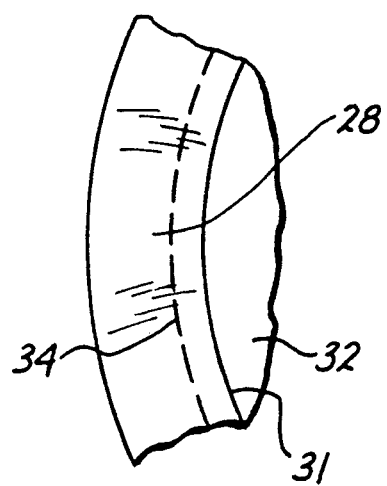
FIG. 4 is a fragmentary bottom elevational view of the lens device shown in FIG. 1.

Referring now to the drawings, FIGS. 1, 3 and 4 show a corneal onlay lens, shown generally at 10, attached to a cornea 12. Lens 10 includes a central circular, optically clear optic 14, which is configured to correct the vision of the patient to whose cornea lens 10 is attached, and a flange or wing, shown generally at 16, which extends generally radially outwardly from optic 14 and optical or radial axis 18 of lens 10.

More specifically, lens 10 is made, e.g., molded, as a unitary component of a synthetic polymeric material, e.g., polymethyl methacrylate. Optic 14 includes an anterior surface 20 and a posterior surface 22, which abuts the upper or anterior surface 24 of cornea 12. Upper surface 24 may not be the original or naturally occurring upper surface of cornea 14. In order to prepare the cornea 14 for implantation of lens 10, the naturally occurring upper surface of the cornea 14 may be removed, e.g., abraded away. In any event, the posterior surface 22 of optic 14 abuts cornea 12.

Flange 16 includes an anterior surface 26, which is substantially a continuation of anterior surface 20 of optic 14, a concave bottom surface 28, a connecting surface 30, and a posterior surface 32, which is substantially a continuation of posterior surface 22 of optic 14. Anterior surface 26 and bottom surface 28 come together at edge or line 29, while bottom surface 28 and connecting surface 30 come together at edge or line 31. Connecting surface 30 and posterior surface 32 come together at edge or line 34 and together form a generally V-shaped flute which extends generally inwardly toward an optical axis 18. The angle defined by this flute, i.e., connecting surface 30, line 34 and posterior surface 32, is more preferably in the range of about 30° to about 60°.

Lens 10 is attached to cornea 12 as follows. Cornea 12 is prepared to receive lens 10 by cutting a circular groove in cornea 12. This circular groove, the cutting of which can be accomplished by conventional and well known instruments, is preferably positioned at an angle extending outwardly from the center of cornea 12. This groove forms an outer flap 36 of corneal tissue. A second circular groove is cut in cornea 12, preferably positioned at an angle extending inwardly toward the center of cornea 12. This second groove forms an inner flap 38 of corneal tissue. Further, it may be desireable to remove a quantity of corneal tissue from between these two grooves in order to better accommodate lens 10.

Also, as noted previously, the original or naturally occurring outer surface, or portion thereof, of cornea 12 may be removed in anticipation of attaching lens 10 to cornea 12.

Figure 2:
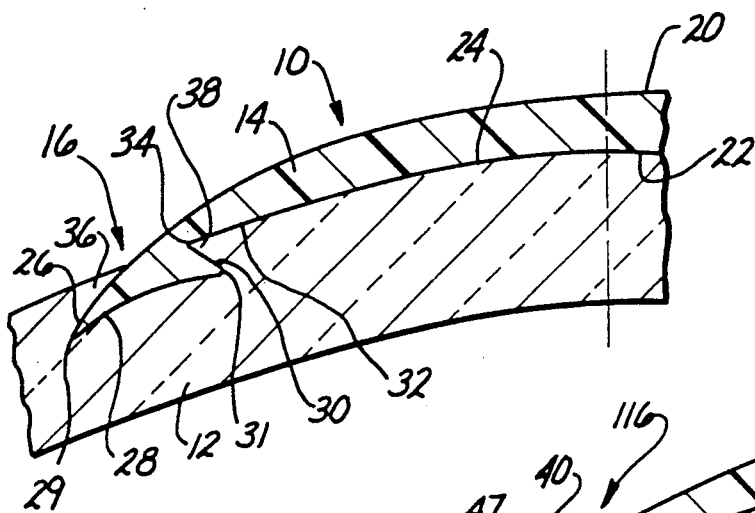
FIG. 2 is an enlarged fragmentary cross-sectional view of the lens device and cornea shown in FIG. 1.

Once cornea 12 has been prepared, lens 10 is placed with respect to cornea 12 so that anterior surface 26, bottom surface 28 and connecting surface 30 of flange 16 are captured within the grooves cut in cornea 12. This placement of lens 10 is substantially as shown in FIGS. 1 and 2. With lens 10 so placed, outer flap 36 overlays anterior surface 26 and inner flap 38 overlays connecting surface 30. This "double overlaying" arrangement provides for very effective initial and final attachment of lens 10 to cornea 12. In other words, this arrangement reduces, and may eliminate, the need for suturing lens 10 to cornea 12 at the time lens 10 is surgically associated with cornea 12 and provides resistance to forces tending to remove lens 10 from cornea 12 after the cornea 12 has grown around lens 10. If desired, lens 10 may be sutured in place in cornea 12, using conventional techniques.

The combination of the outer flap 36 and inner flap 38 overlaying portions of flange 16 provides for resistance to forces both parallel to the radial axis 18 and substantially parallel to anterior surface 20 of optic 14 tending to displace or remove lens 10 from cornea 12. Such forces may occur as the result of the blinking of an eyelid over lens 10, and/or the movements of the patient's head as he/she goes about every day activities.

Figure 5:
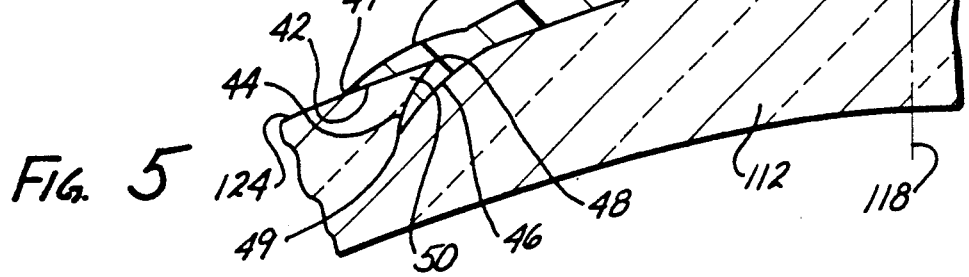
FIG. 5 is an enlarged, fragmentary cross-sectional view of another lens device according to the present invention shown attached to a cornea.

Another corneal onlay lens, shown generally at 110, is illustrated in FIG. 5. Except as expressly set forth below, lens 110 is structured, functions, and is attached to a cornea substantially similarly to lens 10, as described herein. Components of lens 110 which correspond to components of lens 10 are given corresponding reference numerals increased by 100.

Corneal onlay lens 110, attached to cornea 112, includes a central, circular optic 114 and a flange shown generally at 116. The primary difference between lenses 10 and 110 is in the structure of the flange. In lens 110, flange 116 includes an anterior surface 40, a first interior surface 42, and second interior surface 44 and a posterior surface 46. Anterior surface 40 and first interior surface 42 come together at edge or line 47. First and second interior surfaces 42 and 44 come together at line 48 and together form a generally V-shaped flute which extends generally outwardly away from optical axis 118. The angle defined by this flute, i.e., first interior surface 42, line 48 and second interior surface 44, is more preferably in the range of about 30° to about 60°. Second interior surface 44 and posterior surface 46 come together at edge or line 49. The area of each of first interior surface 42 and second interior surface 44 is larger than the area of at least one surface in flange 116 parallel to optical axis 118 of lens 110. Also, the surface defined by lines 47 and 49 has an area larger than the area of at least one surface in flange 116 parallel to optical axis 118.

Lens 110 is attached to cornea 112 as follows. Cornea 112 is prepared to receive lens 110 by cutting a circular groove in cornea 112 which extends at an angle outwardly from the center of cornea 112. This groove forms a flap 50 of corneal tissue.

Once cornea 112 has been prepared, lens 110 is placed with respect to cornea 112 so that the leg of flange 116 defined by second interior surface 44 and posterior surface 46 is located in the groove previously cut. First interior surface 42 is located in abutting relationship to the upper surface 124 of cornea 112. This placement of lens 110 relative to cornea 112 is shown in FIG. 5.

With lens 110 so placed, flap 50 overlays second interior surface 44 and is captured by the flute defined by first and second interior surfaces 42 and 44 and line 48. With flap 50 being situated in this overlying and captured relationship very effective initial and final attachment of lens 110 to cornea 112 is provided. This arrangement reduces, and may eliminate, the need for suturing the lens 110 to cornea 112 during the surgical implantation. After cornea 112 grows around or adheres to lens 110, substantial resistance is provided against forces tending to remove lens 110 from cornea 112. With flap 50 in the overlaying and captured relationship noted above, resistance to forces both parallel to optical axis 118 and substantially parallel to anterior surface 120 of optic 114 is provided.

Figure 6:
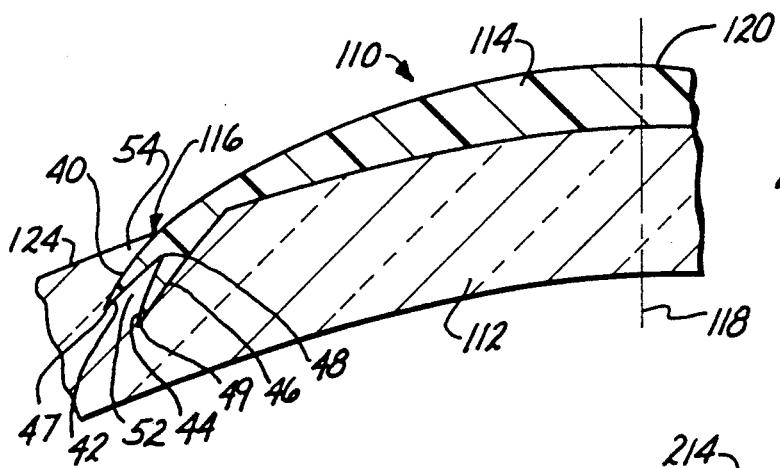
FIG. 6 is an enlarged fragmentary cross-sectional view of the lens device shown in FIG. 5 attached to a cornea in a different manner.

FIG. 6 illustrates an alternate approach to attaching lens 110 to cornea 112. In this approach, cornea 112 is prepared to receive lens 110 by cutting two circular grooves in cornea 112 each of which extends at a different angle outwardly from the center of cornea 112. These two grooves form an inner flap 52 of corneal tissue therebetween. In addition, the uppermost groove forms an outer flap 54 of corneal tissue.

Once cornea 112 has been prepared, lens 110 is placed with respect to cornea 112 so that the leg of flange 116 defined by anterior surface 40 and first interior surface 42 is located in the uppermost groove and the leg of the flange 116 defined by second interior surface 44 and posterior surface 46 is located in the lowermost groove in cornea 112. This placement of lens 110 relative to cornea 112 is shown in FIG. 6.

With lens 110 so placed, outer flap 54 overlays anterior surface 40 of flange 116 and inner flap 52 is captured by the flute defined by first and second interior surfaces 42 and 44 and line 48. The outer portion of flange 116 is completely surrounded by corneal tissue so that very effective initial and final attachment of lens 110 to cornea 112 is provided. This arrangement reduces, and may eliminate, the need for suturing the lens 110 to cornea 112 during surgical implantation. After cornea 112 grows around or adheres to lens 110, substantial resistance is provided against forces tending to remove lens 110 from cornea 112. With cornea 112 completely surrounding the outer portion of flange 116, as noted above, resistance to forces parallel to optical axis 118 and substantially parallel to anterior surface 112 of optic 114 tending to displace or remove lens 110 from cornea 112 is provided.

Figure 7:
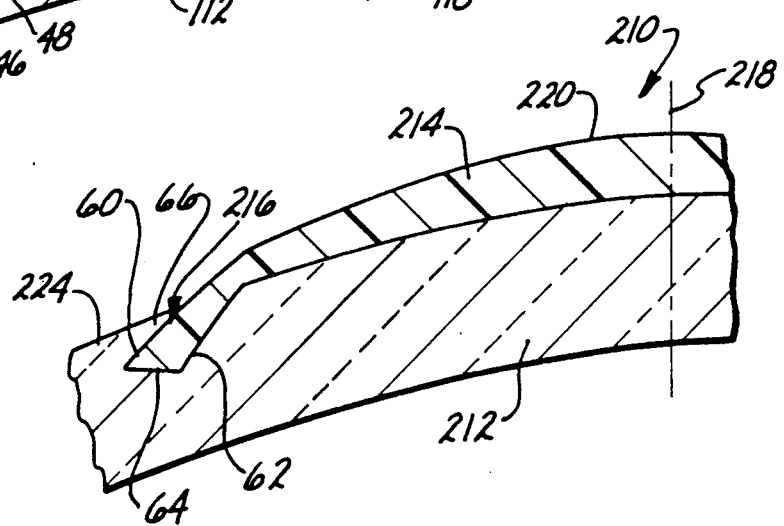
FIG. 7 is an enlarged, fragmentary cross-sectional view of an alternate lens device according to the present invention shown attached to a cornea.

An alternate corneal onlay lens, shown generally at 210, is illustrated in FIG. 7. Except as expressly set forth below, lens 210 is structured, functions and is attached to a cornea substantially similarly to lens 10, as described herein. Components of lens 210 which correspond to components of lens 10 are given corresponding reference numerals, increased by 200.

The primary difference between lens 10 and lens 210 involves the structure of flange 216. Lens 210 includes a flange 216 which has an anterior surface 60, a posterior surface 62 and a third surface 64 which joins the other two surfaces. This third surface 64 is generally frustoconical in configuration, extending generally away from optical axis 218 going from posterior surface 62 to anterior surface 60. In addition, the area of this third surface 64 is larger than the area of at least one surface in flange 216 parallel to optical axis 218. In the embodiment illustrated in FIG. 7, the areas of surfaces in flange 216 parallel to third surface 64 progressively and substantially continuously increase so that third surface 64 itself has the largest area of any of such surfaces.

Cornea 212 is prepared to receive lens 210 by cutting a circular groove or grooves in cornea 212. Further, it may be desirable to remove a quantity of corneal tissue adjacent to the groove or from between the grooves to better accommodate lens 210. In any event, such groove or grooves form a corneal flap 66.

Once cornea 212 has been prepared, lens 210 is placed with respect to cornea 212 so that anterior surface 60, posterior surface 62 and third surface 64 are captured within the groove or grooves cut in cornea 212. This placement of lens 210 is substantially as shown in FIG. 6. With lens 210 so placed, corneal flap 66 overlays anterior surface 60. This overlaying arrangement together with the frustoconical configuration of the relatively large third surface 64 provides for very effective initial and final attachment of lens 210 to cornea 212. The need to suture lens 210 in place is reduced, and may be eliminated. The thus attached lens 210 is resistant to displacement or removal from cornea 212 by forces acting parallel to the optical axis 218 and substantially parallel to anterior surface 220 of optic 214.

Referring now to FIGS. 8 and 9, an additional corneal onlay lens, shown generally at 70, includes a central circular optic 72, a flange or wing 74 and a radial axis 76. Optic 72 is configured to correct the vision of the patient to whose cornea it is attached. Flange 74 extends generally radially outwardly from optic 72 and optical axis 76 of lens 70.

Flange 74 includes a plurality of through holes 78 or fenestrations which have substantially the same size, e.g., diameter, and are substantially uniformly spaced apart on, around, flange 74. Through holes 78 are sized to allow or provide for the growth of corneal tissue therethrough.

Lens 70 is made, e.g., molded, as a unitary component of a synthetic hydrogel-forming polymeric material, e.g., polyhydroxyethyl methacrylate. Such materials are very effective in-producing corneal onlay lenses. One drawback that has occurred is that such hydrogel-forming materials tend to have reduced strength. This feature, in turn, makes attaching the lens to the cornea somewhat difficult. For example, sutures which are used to attach the lens to the cornea may break through the relatively weak hydrogel lens and become ineffective to hold the lens in place.

The lens 70 overcomes these difficulties by providing a flange 74 which has increased unit strength relative to the optic 72. With flange 74 being relatively strong, the likelihood of attaching sutures penetrating through flange 72 is reduced. This, in turn, provides for more secure initial attachment of lens 70 to the cornea.

One particularly useful approach to providing a flange 74 having increased unit strength is to selectively increase the cross-linking of the polymeric material making up the flange 70. Increasing the degree of cross-linking in flange 70 can be achieved by chemical means, e.g., increasing the concentration of cross-linking components, e.g., multifunctional compounds, in flange 70, and/or by selectively subjecting flange 70 to radiation, e.g., ultraviolet light and/or gamma-ray radiation. In any event, flange 74 has increased unit strength relative to optic 72. Flange 74 includes an anterior surface 80, a posterior surface 82, and an outer surface 84.

Referring to FIG. 9, lens 70 is attached to cornea 86 as follows. Cornea 86 is prepared to receive lens 70 by cutting a circular groove in cornea 86 which extends from the anterior surface 88 of cornea 86 at an angle outwardly from the center of cornea 86. This groove forms a flap 89 of cornea tissue.

Once cornea 86 has been prepared, lens 70 is placed with respect to cornea 86 so that flange 74, and in particular each of the through holes 78, is located in the groove. In this manner, flap 89 overlays each of the through holes 78. This placement of lens 70 relative to cornea 86 is as shown in FIG. 9.

With lens 70 so placed, flap 89 overlays flange 74 and through holes 78. Using conventional techniques, lens 70 is sutured in place by a plurality of individual sutures 90, one of which is illustrated in FIG. 9. Each suture 90 is passed through flap 89 and a through hole 78. The suture 90 is then passed below the posterior surface 82 of flange 74 and up out of the anterior surface 88 of cornea 86. The two ends of suture 90 are then tied together.

This suturing provides for secure initial attachment of lens 70 to cornea 86. Further, the overlaying relation of flap 89 to flange 74 provides additional protection or resistance against forces, both parallel to the optical axis 71 of lens 70 and substantially parallel to the anterior surface 92 of optic 72 tending to displace or remove lens 70 from cornea 86.

After the initial attachment of lens 70 to cornea 86, a period of healing ensues. During this period, corneal tissue grows into and through each of the through holes 78. This growth, in effect, connects flap 89 to the main body of cornea 86 through through hole 78. After such growth, cornea 86 effectively has grown around flange 74 and provides for very effective permanent attachment of lens 70 to cornea 86. Thus, after the sutures 90 are removed, lens 70 is securely attached to cornea 86 and is resistant to being displaced or removed by forces, e.g., from directions as described above.

A further corneal onlay lens, shown generally at 170, is illustrated in FIGS. 10 and 11. Except as expressly set forth below lens 170 is structured, functions and is attached to a cornea substantially similarly to lens 70, as described herein. Components of lens 170 which correspond to components of lens 70 are given corresponding reference numerals increased by 100.

The primary difference between lens 70 and lens 170 involves the structure of flange 174. In lens 170, flange 174 includes a plurality of areas 94 of reduced thickness extending between each of the through holes 178 and the outer surface 184. Each of these areas 94 extends downwardly from the anterior surface 180 of flange 174. This allows relatively easy access to such areas 94 should such access become necessary, as described below.

Areas 94 of reduced thickness also have reduced strength relative to the rest or remainder of the solid flange 174. Such areas 94 make it more easy to remove lens 170 from cornea 186 when necessary. To illustrate, when it is desired to remove lens 170 from cornea 186, areas 94 can be relatively easily cut or torn to facilitate this removal. Thus, lens 170 provides substantially all of the advantages of lens 70, e.g., as described herein, and, in addition, provides for relatively easy surgical removal from cornea 186, should such removal become necessary or desirable.

While this invention has been described with respect to various specific examples and embodiments, it is to be understood that the invention is not limited thereto and that it can be variously practiced within the scope of the following claims.

What is claimed is:

1. A lens device for attachment to a cornea, said lens device comprising:
an optic having an optical axis;
a flange coupled to the optic and extending radially outwardly of the optic;
said flange including first and second radially extending projections adapted for use in attaching the lens device to the cornea, portions of said projections lying in the same axial plane and on the same side of the optical axis; and
said first projection extending radially outwardly.

2. A lens device as described in claim 1 wherein said second projection extends radially outwardly.

3. A lens device as described in claim 1 wherein the first and second projections define a generally V-shaped flute which opens radially outwardly.

4. A lens device as described in claim 3 wherein the flange circumscribes the optic and has an anterior surface on an anterior side of the first projection, a first inner surface on a posterior side of the first projection, a second inner surface on an anterior side of the second projection and a posterior surface on a posterior side of the second projection.

5. The lens device of claim 3 wherein said generally V-shaped flute defines an angle of less than about 90°.

6. A lens device as described in claim 1 wherein the second projection extends radially inwardly.

7. A lens device as described in claim 6 wherein the flange has a posterior surface and the second projection and the posterior surface define a V-shaped flute which opens radially inwardly.

8. A lens device as described in claim 6 wherein the flange circumscribes the optic and the optic has an anterior surface, the flange has an anterior surface which is a continuation of the anterior surface of the optic, first and second posterior surfaces axially offset from each other and a connecting surface between the first and second posterior surfaces, the optic has a posterior surface and the second posterior surface forms a continuation of the posterior surface of the optic, said anterior surface of the flange and the first posterior surface defining the first projection and the connecting surface and the first posterior surface defining the second projection, the connecting surface and the second posterior surface defining an angle of less than about 90 degrees.

9. A lens device for attachment to a cornea, said lens device comprising:
an optic having an optical axis;
a flange coupled to the optic and extending radially outwardly of the optic;
said flange including a radially inwardly extending projection adapted for use in attaching the lens device to the cornea; and
the flange having a posterior surface and the radiallly inwardly projection and the posterior surface defining a V-shaped flute which opens radially inwardly.

10. A method for attaching a lens device to the cornea of an eye comprising:
providing an optic having an optical axis and a flange coupled to the optic and extending radially outwardly of the optic with the flange including a radially inwardly extending projection which cooperates with a surface of the lens device to define a generally V-shaped flute which opens radially inwardly; and placing the lens device on the cornea with the projection being received in the cornea so that a region of the cornea overlies the projection and with the V-shaped flute receiving a region of the cornea.

11. A method as defined in claim 10 wherein said surface includes a posterior surface of the flange and said step of placing is carried out so that the posterior surface of the flange overlies the outer surface of the cornea.

12. A method as defined in claim 10 wherein the flange includes a radially outwardly extending projection and said step of placing includes placing the radially outwardly extending projection into the cornea with a region of the cornea overlying the radially outwardly extending projection.

13. A method for attaching a lens device to the cornea of an eye comprising:

providing an optic having an optical axis and a flange coupled to the optic and extending radially outwardly of the optic with the flange including first and second radially extending projections adapted for use in attaching the lens device to the cornea and with portions of said projections lying in the same axial plane and on the same side of the optical axis; and placing the lens device on the cornea with the first projection being received in the cornea so that a region of the cornea overlies the first projection and with the second projection contacting the cornea anteriorly of the first projection.

14. A method as defined in claim 13 wherein the second projection overlies the outer surface of the cornea.

15. A method as defined in claim 13 wherein the second projection is embedded in the cornea.

16. A method of attaching a lens device to the cornea of a patient comprising:

placing a lens device having an optic configured for correction of the patient's vision, a flange having increased unit strength relative to said optic affixed to and radially extending from the optic and at least one through hole in said flange sized and adapted to provide for growth of corneal tissue therethrough, in association with said cornea so that corneal tissue overlays at least a portion of said flange.

17. The method of claim 16 wherein said corneal tissue overlays at least a portion of said through hole.

18. The method of claim 16 wherein said corneal tissue overlays substantially all of said through hole.

19. The method of claim 16 wherein said flange includes a plurality of said through holes.

20. The method of claim 19 wherein said lens device is placed so that corneal tissue overlays substantially all of said through holes.

21. The method of claim 16 wherein said flange has a outer periphery and includes one area of reduced strength located between said through hole and said outer periphery of said flange.

22. The method of claim 19 wherein said flange has an outer periphery and includes a plurality of areas of reduced strength located between said through holes and said outer periphery of said flange.

23. The method of claim 16 wherein said flange has a outer periphery and includes an area of reduced thickness located between said through hole and said outer periphery of said flange.

24. The method of claim 19 wherein said flange has an outer periphery and includes a plurality of areas of reduced thickness located between said through holes and said outer periphery of said flange.

25. The method of claim 16 which further comprises preparing said cornea to receive a portion of said lens device prior to said placing.

26. A lens device for attachment to the cornea of a patient comprising:

an optic for correction of the patient's vision;

a flange affixed to and radially extending from said optic, said flange having an increased unit strength relative to said optic; and at least one through hole in said flange sized and adapted to provide for growth of corneal tissue therethrough.

27. The lens device of claim 26 which comprises a plurality of said through holes.

28. The lens device of claim 27 wherein said through holes are substantially uniformly spaced on said flange.

29. The lens device of claim 26 wherein said flange has an outer periphery and includes one area of reduced strength located between said through hole and said outer periphery of said flange.

30. The lens device of claim 27 wherein said flange has an outer periphery and includes a plurality of areas of reduced strength located between said through holes and said outer periphery of said flange.

31. The lens device of claim 26 wherein said flange has an outer periphery and includes one area of reduced thickness located between said through hole and said outer periphery of said flange.

32. The lens device of claim 27 wherein said flange has an outer periphery and includes a plurality of areas of reduced thickness located between said through holes and said outer periphery of said flange.

33. The lens device of claim 31 wherein the flange has an anterior surface and said area of reduced thickness adjacent said anterior surface.

34. The lens device of claim 32 wherein the flange has an anterior surafce and said plurality of areas of reduced thickness are adjacent said anterior surface.

35. The lens device of claim 26 made of a hydrogel-forming material.

36. The lens device of claim 26 wherein said flange is conditioned to increase its strength.

37. The lens device of claim 26 wherein said flange is chemically conditioned to increase its strength.

38. The lens device of claim 26 wherein said flange is exposed to radiation to increase its strength.

39. The lens device of claim 26 made of a synthetic polymeric material and said flange is conditioned to increase the degree of cross-linking of said synthetic polymeric material in said flange.

* * * * *